United States Patent
Way

(10) Patent No.: US 9,561,359 B2
(45) Date of Patent: Feb. 7, 2017

(54) MEDICAL CONNECTOR ASSEMBLY

(71) Applicant: Iris Way, Fort Myers, FL (US)

(72) Inventor: Iris Way, Fort Myers, FL (US)

( * ) Notice: Subject to any disclaimer, the term of this patent is extended or adjusted under 35 U.S.C. 154(b) by 0 days.

(21) Appl. No.: 14/324,612

(22) Filed: Jul. 7, 2014

(65) Prior Publication Data
US 2015/0032089 A1 Jan. 29, 2015

Related U.S. Application Data

(60) Provisional application No. 61/859,531, filed on Jul. 29, 2013.

(51) Int. Cl.
*A61M 39/10* (2006.01)
*A61J 15/00* (2006.01)

(52) U.S. Cl.
CPC ........ *A61M 39/1011* (2013.01); *A61J 15/0026* (2013.01); *A61M 2039/1033* (2013.01); *A61M 2039/1094* (2013.01)

(58) Field of Classification Search
CPC ................. A61M 39/1011; A61M 2039/1027; A61M 2039/1077; A61M 2039/1094; A61M 39/10; A61M 2039/1033; A61M 2039/1083; A61M 2039/1088; A61M 39/1055; A61J 15/0026; F16L 37/252
See application file for complete search history.

(56) References Cited

U.S. PATENT DOCUMENTS

| | | | | |
|---|---|---|---|---|
| 3,876,234 A | * | 4/1975 | Harms | A61M 39/10 285/332 |
| 3,918,450 A | * | 11/1975 | Patel | A61M 25/00 604/243 |
| 4,349,024 A | * | 9/1982 | Ralston, Jr. | A61M 39/12 604/403 |
| 4,619,640 A | * | 10/1986 | Potolsky | A61M 39/10 128/912 |
| 5,057,093 A | * | 10/1991 | Clegg | A61M 39/10 128/912 |
| 5,113,571 A | * | 5/1992 | Manska | A61M 39/10 285/332 |
| 5,281,206 A | * | 1/1994 | Lopez | A61M 39/04 604/533 |
| 5,395,348 A | * | 3/1995 | Ryan | A61M 39/14 251/149.1 |

(Continued)

*Primary Examiner* — Imani Hayman
*Assistant Examiner* — James D Ponton
(74) *Attorney, Agent, or Firm* — Tarolli, Sundheim, Covell & Tummino LLP

(57) ABSTRACT

One aspect of the present disclosure relates to a medical connector assembly comprising a male port plug and a female port plug that is releasably lockable with the male port plug. The male port plug can include a first end portion adapted to mate with a fluid source, and a tapered second end portion. The second end portion can include a twistable locking mechanism comprising a plurality of crescent-shaped flanges that extend annularly about less than the entire outer circumferential surface of the second end portion. The female port plug can include a central channel configured to receive the male port plug. The central channel can have a tapered portion adapted to friction fit with the second end portion of the male port plug. The female port plug can further include a receptacle portion adapted to receive the plurality of flanges comprising the locking mechanism.

1 Claim, 6 Drawing Sheets

(56) References Cited

U.S. PATENT DOCUMENTS

| | | | | |
|---|---|---|---|---|
| 7,316,679 B2* | 1/2008 | Bierman | ............... | A61M 39/10 |
| | | | | 128/DIG. 26 |
| 2006/0264814 A1* | 11/2006 | Sage | ................. | A61M 39/1011 |
| | | | | 604/67 |
| 2010/0121313 A1* | 5/2010 | Goode | .............. | A61M 39/0208 |
| | | | | 604/535 |
| 2012/0265143 A1* | 10/2012 | Krumme | .......... | A61M 5/14566 |
| | | | | 604/131 |
| 2012/0326438 A1* | 12/2012 | Robert | .............. | A61M 39/1011 |
| | | | | 285/305 |

* cited by examiner

MEDICAL CONNECTOR ASSEMBLY

RELATED APPLICATION

This application claims the benefit of U.S. Provisional Patent Application Ser. No. 61/859,531, filed Jul. 29, 2013, the entirety of which is incorporated herein by reference for all purposes.

TECHNICAL FIELD

The present disclosure relates generally to connector assemblies for use with a variety of medical instruments, and more particularly to a medical connector assembly for use with an enteral feeding tube.

BACKGROUND

In general, intravenous (IV) fluid administration to a patient involves the gravity or pump-assisted flow of a medical solution from a sterile source container through a sterile IV tubing set to a patient's vein. Usually at least one sterile connection must be made and maintained to effectively and safely transfer the medical solution from the container to the patient. A sterile connection with an IV tubing set can be made in a variety of ways. The traditional and most commonly used fluid flow connection is made using a sharp needle associated with the first connector to pierce a resealable elastomeric septum of a second connector. An alternative method includes using a blunt cannula connector, which typically has a pre-pierced or partially pierced elastomeric septum connector.

A primary concern with any medical tubing connector is the accidental or unintentional disengagement of the connectors. A sharp or blunt cannula can accidentally be pulled out of a reseal. An accidental disconnection can contaminate the cannula of the connector and/or allow the medical solution to spill or drain. In addition to the interruption in the intravenous therapy, accidental disconnection may compromise the sterility and integrity of the IV flow system. Contaminants may be introduced into the IV flow system if the connectors are reconnected without effective disinfecting.

SUMMARY

The present disclosure relates generally to connector assemblies for use with a variety of medical instruments, and more particularly to a medical connector assembly for use with an enteral feeding tube.

One aspect of the present disclosure relates to a medical connector assembly comprising a male port plug and a female port plug that is releasably lockable with the male port plug. The male port plug can include a first end portion adapted to mate with a fluid source, and a tapered second end portion. The second end portion can include a twistable locking mechanism comprising a plurality of crescent-shaped flanges that extend annularly about less than the entire outer circumferential surface of the second end portion. The female port plug can include a central channel configured to receive the male port plug. The central channel can have a tapered portion adapted to friction fit with the second end portion of the male port plug. The female port plug can further include a receptacle portion adapted to receive the plurality of flanges comprising the locking mechanism.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1A:
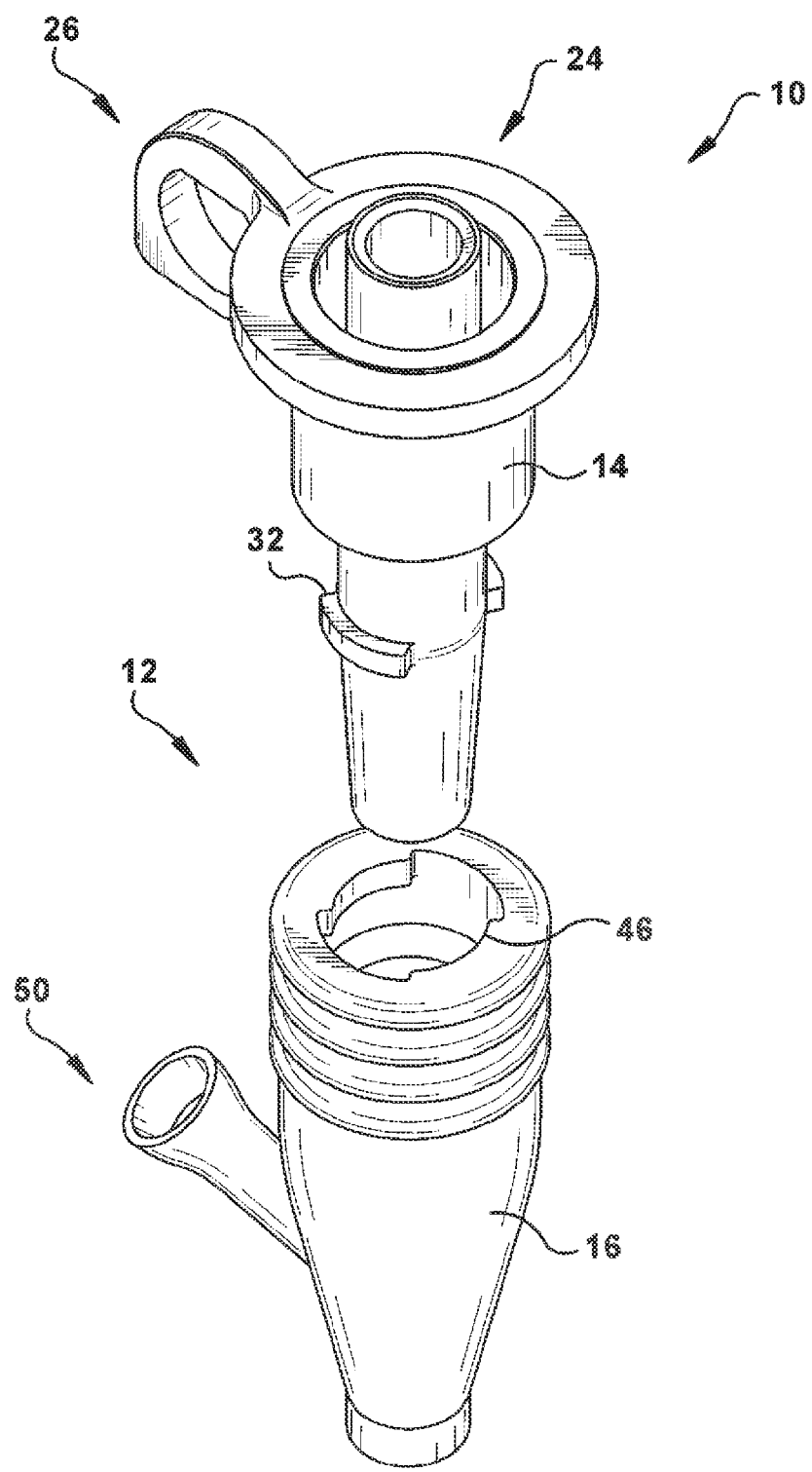
FIGS. 1A-B are perspective views showing a medical connector assembly constructed in accordance with one aspect of the present disclosure.

Unless defined otherwise, all technical and scientific terns used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will he understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Figure 1B:
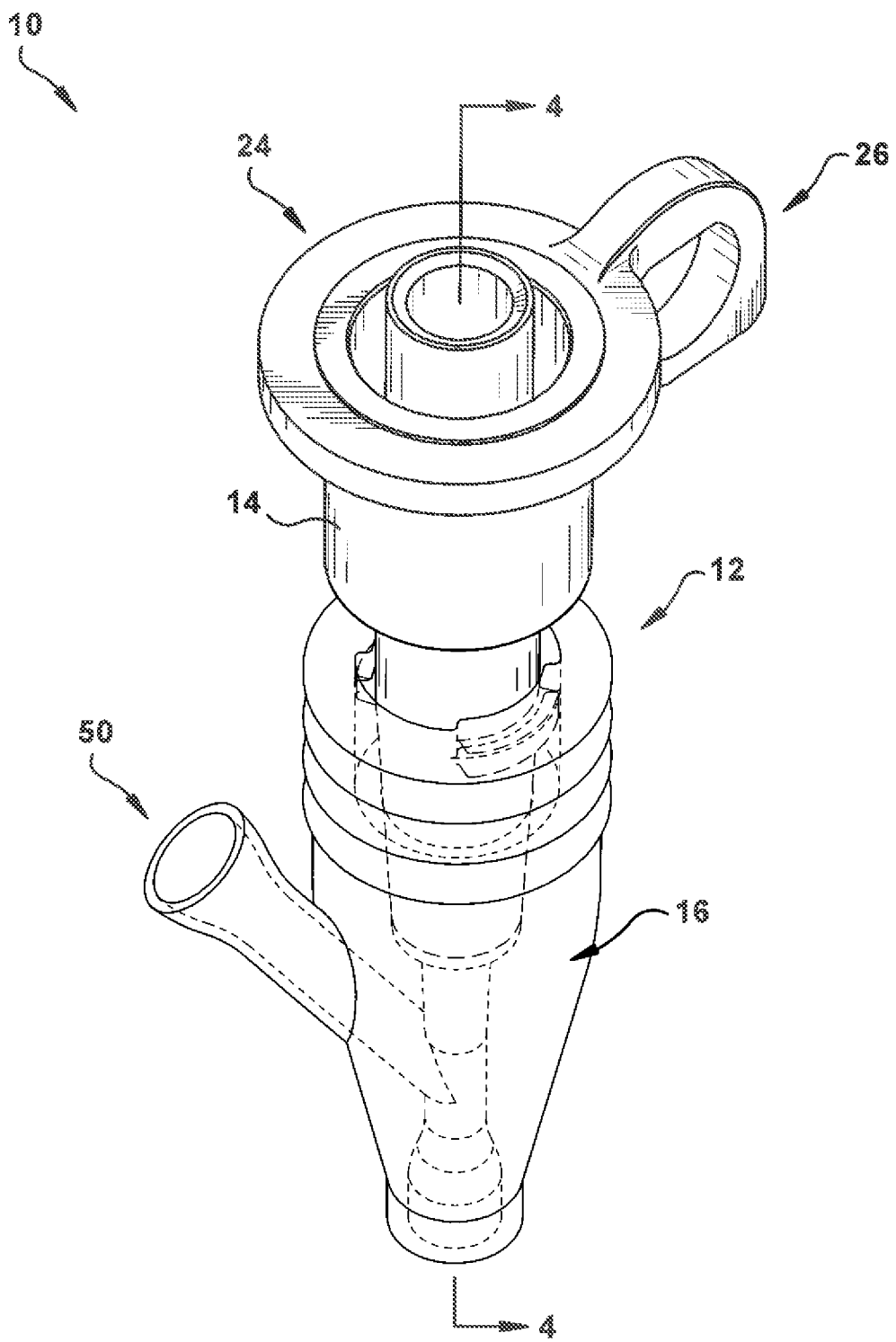

The present disclosure relates generally to connector assemblies for use with a variety of medical instruments, and more particularly to a medical connector assembly for use with an enteral feeding tube. As illustrative of one aspect of the present disclosure, FIGS. 1A-B show a medical connector assembly 10 that can be used to prevent separation or pull-out between various medical instruments. As described in more detail below, the medical connector assembly 10 includes a twistable locking mechanism 12 that promotes symmetrical loading and reduces the amount of motion (e.g., torque) needed to operate (e.g., lock and unlock) the assembly. The locking mechanism 12 is unlike conventional locking elements, which typically include screw connections that unevenly distribute loading and require at least a ½ turn to engage and disengage the locking element. Although the present disclosure is described below in terms of use with enteral feeding tubes, it will be appreciated that the medical connector assembly 10 can find use with any number of medical instruments where a simple, effective, and secure connection between the instruments is desired.

In one aspect of the present disclosure, the medical connector assembly 10 can comprise a male port plug 14 and a female port plug 16 that is releasably lockable with the male port plug. By virtue of the unique construction of the medical connector assembly 10, and in particular the twistable locking mechanism 12, it is possible to produce a releasable form-fit connection between the male and female port plugs 14 and 16. In some instances, the medical connector assembly 10 can be used universally, has an ergonomic shape for ease of handling, and permits a safe but releasable connection between medical instruments. In one example, the medical connector assembly 10 can be used universally with enteral feeding tubes (not shown) and related intravenous feeding systems, is easy to handle, and can be safely connected to associated components of an enteral feeding tube without the danger of accidental loosening of the connection.

Figure 2A:
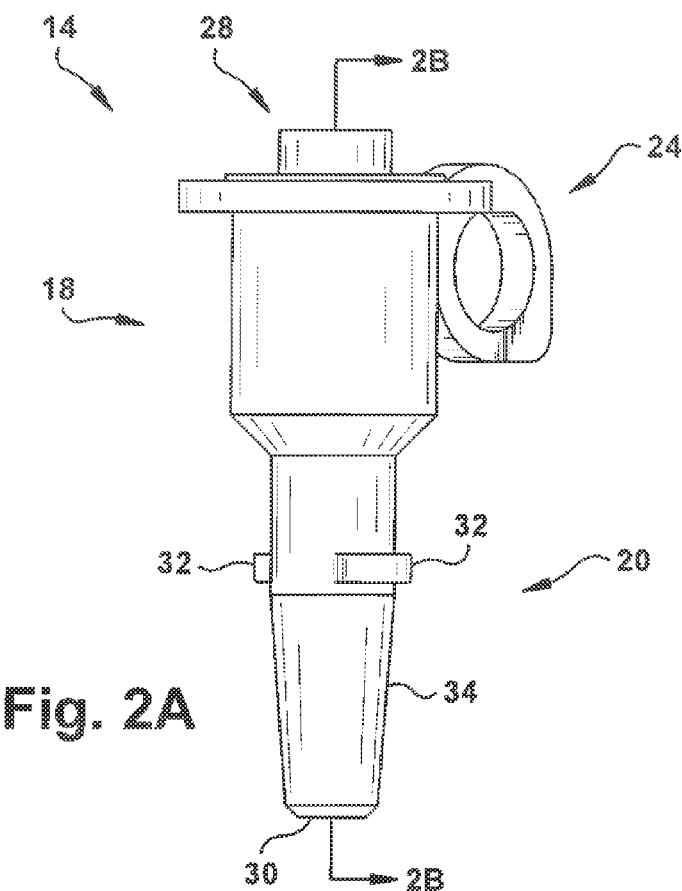
FIG. 2A is a perspective view of a male port plug comprising the medical connector assembly in FIGS. 1A-B.
Figure 2B:
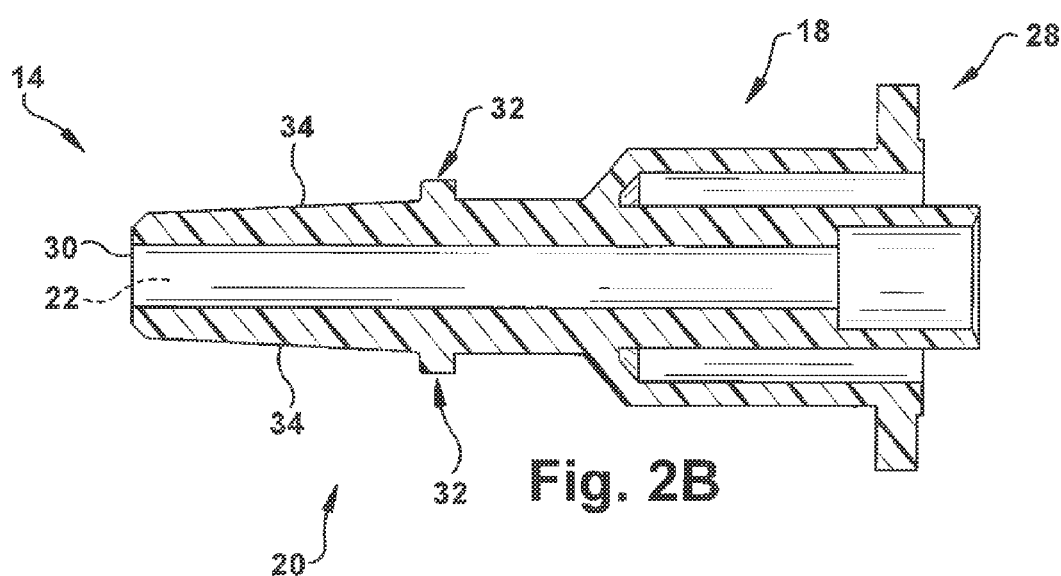
FIG. 2B is a cross-sectional view taken along Line 2B-2B in FIG. 2A.

In another aspect, the male port plug 14 can comprise a first end portion 18, a tapered second end portion 20, and a channel 22 or lumen (FIGS. 2A-B) extending between the first and second end portions. The first end portion 18 is adapted to mate with a fluid source (not shown),such as a syringe, medical tubing, etc. As shown in FIGS. 2A-B, the first end portion 18 has a cylindrical shape with a circular cross-sectional profile. It will be appreciated that the first end portion 18 can have other shapes, such as square, ovoid, etc. The male port plug 14 further includes a closure cap 24 used to close the male port plug and which, by way of a tab 26, is permanently secured to the first end portion 18. In some instances, the closure cap 24 can have a flattened, disc-like shape. The closure cap 24 can further include an attachment funnel 28 for attachment to the fluid source. In some instances, the attachment funnel 28 has a cylindrical shape and includes a lumen (not shown in detail) that is in fluid communication with the channel 22 of the male port plug 14 when the closure cap is mated with the first end portion 18. The dimensions of the attachment funnel 28 can he varied to accommodate the particular configuration of the fluid source.

The second end portion 20 of the male port plug 14 has a conical shape that tapers from the first end portion 18 to an end 30 of the male port plug. The second end portion 20 includes a plurality of crescent-shaped flanges 32 that extend annularly about less than the entire outer circumferential surface 34 of the second end portion. As described below, the flanges 32 form part of the twistable locking mechanism 12. The flanges 32, in addition to other components of the locking mechanism 12, make loading symmetric and reduce the required turn from ½ to ¼. The male port plug 14 can be made of one or a combination of materials, such as rigid polyurethane, rigid polyvinyl chloride (PVC), acrylonitrile butadiene styrene (ABS) or polycarbonate. In some instances, the entire male port plug 14 (e.g., including the closure cap 24) can be made of the same material(s). In other instances, the closure cap 24 can be made of a different material (or materials) than the remainder of the male port plug 14.

Figure 3A:
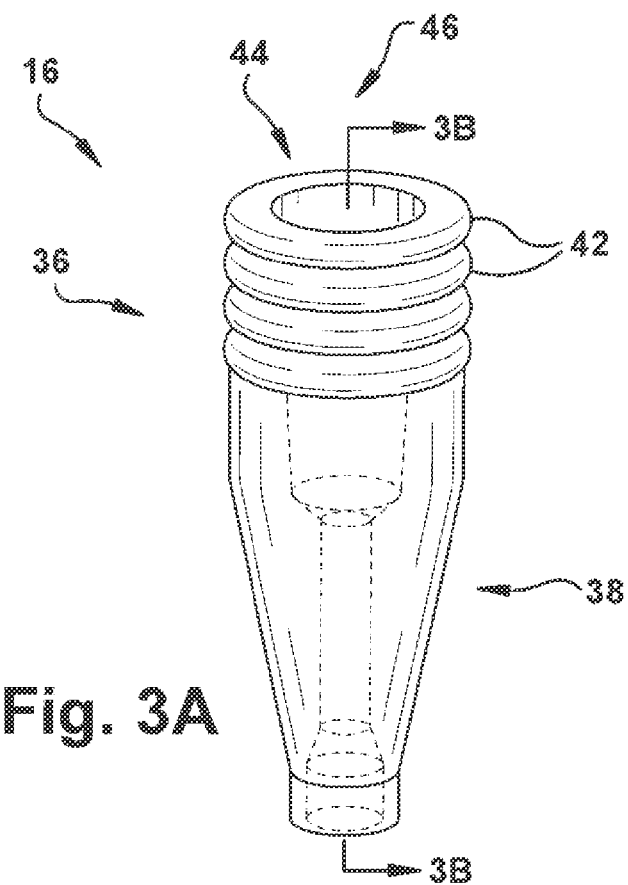
FIG. 3A is a perspective view of a female port plug comprising the medical connector assembly in FIGS. 1A-B.
Figure 3B:
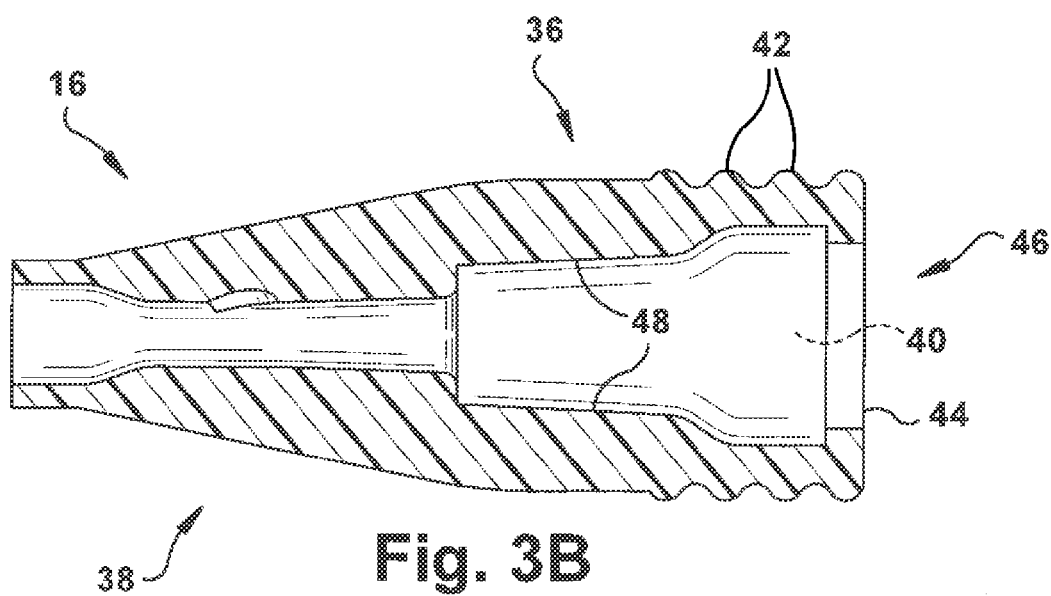
FIG. 3B is a cross-sectional view taken along Line 3B-3B in FIG. 3A.

In another aspect, the female port plug 16 (FIGS. 3A-B) can include a first end portion 36, a second end portion 38, and a channel 40 or lumen extending between the first and second end portions. The first end portion 36 has a cylindrical shape and includes a plurality of circumferential ridges 42, which can assist a user in gripping or holding the female port plug 16 and/or the medical connector assembly 10. Although four ridges 42 are shown in. FIGS. 3A-B, it will be appreciated that the female port plug 16 can include a lesser or greater number of ridges. A first end 44 of the female port plug 16 includes a receptacle portion 46 adapted to receive the flanges 32 comprising the locking mechanism 12. As shown in FIG. 1A, the receptacle portion 46 has a bow-shaped cross-sectional profile that permits easy ingress and egress of the male port plug 14. The channel 40 of the female port plug 16 has a tapered or conical shape and is configured to receive the second end portion 20 of the male port plug 14. In particular, a tapered mating portion 48 of the channel 40 is shaped and dimensioned to accommodate the tapered shape of the second end portion 20 of the male port plug 14 and thereby form a friction fit therebetween. When the male and female port plugs 14 and 16 are securely mated with one another, a fluid tight seal is formed between respective portions thereof (indicated by circled areas in FIG. 4).

The female port plug 16 further includes at least one side port 50. The side port 50 can have a tubular configuration and be integrally formed with the female port plug 16. The side port 50 can have a first end 52 that is oppositely disposed from a second end 54. A channel 56 or lumen extends between the first and second ends 52 and 54. The channel 56 or lumen can be in fluid communication with the channel 40 of the female port plug 16. The first end 52 of the side port 50 can include an opening adapted to receive a fluid source, such as a syringe or medical tubing. The second end 54 can be integrally formed with a side wall of the female port plug 16. In some instances, the side port 50 can be made of the same material(s) as the rest of the female port plug 16. The dimensions of the side port 50 can be varied depending upon the intended use of the medical connector assembly 10.

Figure 4:
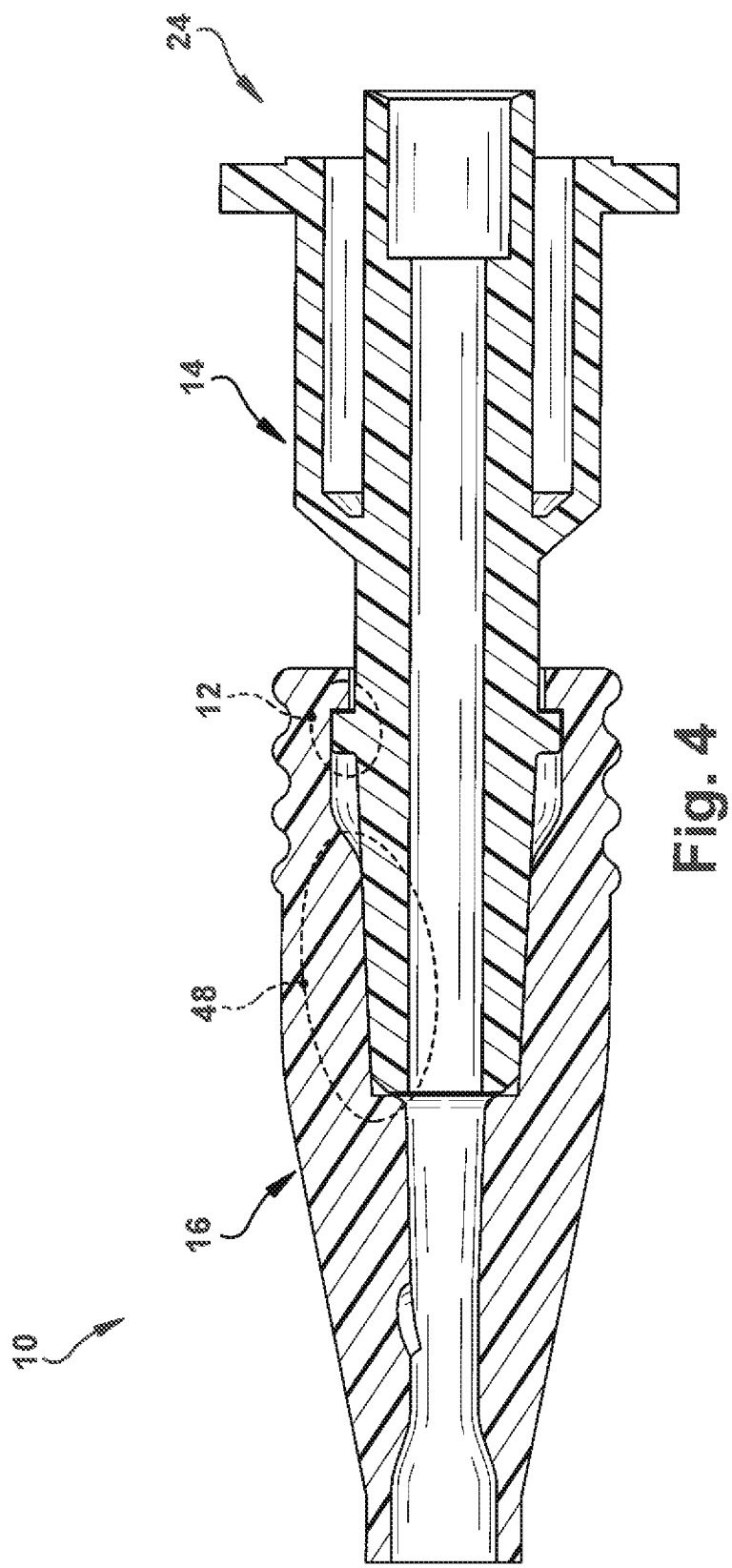
FIG. 4 is a cross-sectional view taken along Line 4-4 in FIG. 1B.
Figure 5:
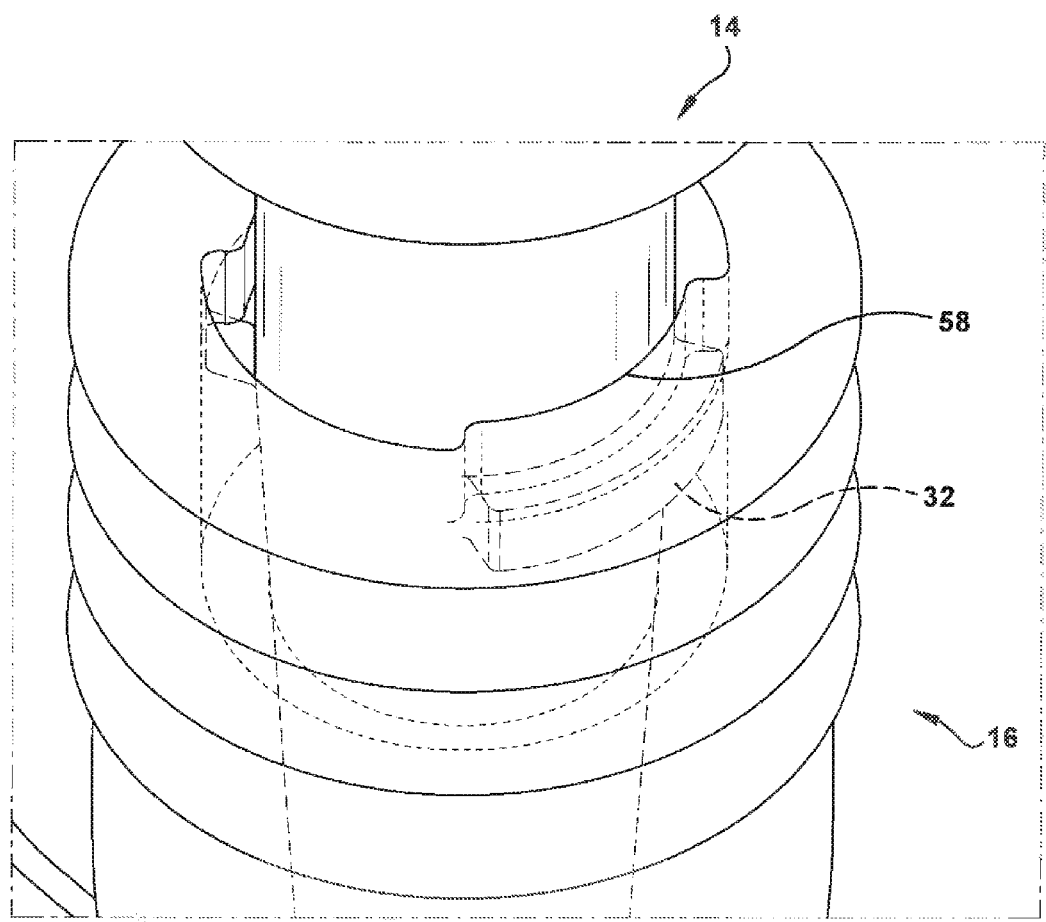
FIG. 5 is magnified perspective view of a twistable locking mechanism comprising the medical connector assembly in FIGS. 1A-B.

Operation of the medical connector assembly 10, and in particular the locking mechanism 12, is illustrated in FIGS. 4-5. To securely mate the male and female port plugs 14 and 16 so that a fluid-tight seal is formed therebetween, the second end portion 20 of the male port plug 14 is inserted into the channel 40 of the female port plug 16. Before insertion, however, the flanges 32 of the male port plug 14 are aligned with the receptacle portion 46 of the female port plug 16 so that the flanges can readily pass therethrough. The male port plug 14 is then urged into the channel 40 of the female port plug 16 until the outer circumferential surface 34 thereof is friction fit with the surface defining the channel of the female port plug. The channel 22 of the male port plug 14 and the channel 40 of the female port plug 16 are brought into fluid communication with one another. Simultaneously, the flanges 32 of the male port plug 14 pass through the corresponding portions of the receptacle portion 46 into the channel 40 of the female port plug 16. Once the male port plug 14 is friction fit within the female port plug 16, the male port plug or the female port plug is rotated by a ¼ turn in either a clock-wise or counter-clockwise direction. Rotating either of the male port plug 14 or the female port plug 16 causes each of the flanges 32 to engage a corresponding lip 58 of the receptacle portion 46 of the female port plug. With the flanges 32 securely engaged with the respective lips 58 of the receptacle portion 46 (FIGS. 4-5), undesirable separation or pull-out of the male and female port plugs 14 and 16 is prevented.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. A medical connector assembly consisting of:
   a male port plug including a first end portion adapted to mate with a fluid source and a tapered second end portion, the second end portion including a twistable locking mechanism free from screw connections and having a plurality of crescent-shaped flanges that extend annularly about less than an entire outer circumference of the second end portion;
   a female port plug that is releasably lockable with the male port plug, the female port plug including a central channel that receives the male port plug, the central channel having a tapered portion that friction fits with the second end portion of the male port plug, the female port plug further including a receptacle portion that is free from screw connections and receives the plurality of flanges of the locking mechanism; and
   a tubular side port integrally formed with the female port plug, the side port including a channel that is in fluid communication with the central channel of the female port plug;
   wherein the male port plug can be rotated about the central channel relative to the female port plug to move the locking mechanism between a fully locked position in which the male and female port plugs are sealingly mated and incapable of separation, and a fully unlocked position in which the male and female port plugs are not sealingly mated and capable of separation.

* * * * *